(12) United States Patent
Irie et al.

(10) Patent No.: US 7,054,929 B2
(45) Date of Patent: May 30, 2006

(54) COMMUNICATION SYSTEM, INFORMATION AGENT METHOD AND RECORDING MEDIUM

(75) Inventors: Hiroyuki Irie, Kawasaki (JP); Takashi Nishida, Kawasaki (JP); Takayuki Kamoto, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 626 days.

(21) Appl. No.: 09/893,903

(22) Filed: Jun. 29, 2001

(65) Prior Publication Data

US 2002/0107976 A1 Aug. 8, 2002

(30) Foreign Application Priority Data

Feb. 2, 2001 (JP) ............................. 2001-026612

(51) Int. Cl.
*G06F 15/173* (2006.01)
(52) U.S. Cl. ...................................... 709/225; 709/229
(58) Field of Classification Search ........ 709/217–219, 709/225, 229; 705/1; 713/200–202
See application file for complete search history.

(56) References Cited

U.S. PATENT DOCUMENTS

| | | | |
|---|---|---|---|
| 5,725,384 A | | 3/1998 | Ito et al. |
| 6,018,713 A | * | 1/2000 | Coli et al. .................. 705/2 |
| 6,148,297 A | * | 11/2000 | Swor et al. ................. 707/3 |
| 6,283,923 B1 | * | 9/2001 | Finkelstein et al. ......... 600/532 |
| 6,466,956 B1 | * | 10/2002 | Cho et al. ................... 715/531 |
| 6,658,483 B1 | * | 12/2003 | Iwamoto et al. ............ 709/246 |

FOREIGN PATENT DOCUMENTS

| | | |
|---|---|---|
| JP | 8-292937 | 11/1996 |
| JP | 11-175617 | 7/1999 |
| JP | 11-250165 | 9/1999 |
| JP | 2001-026612 | 1/2001 |

OTHER PUBLICATIONS

Toshiaki Atsumoto, "Home page", Nikkei Multimedia, Nikkei Business Publications Inc., No. 47, p. 112-115.

* cited by examiner

*Primary Examiner*—Larry D. Donaghue
(74) *Attorney, Agent, or Firm*—Staas & Halsey LLP

(57) ABSTRACT

A communication system for efficient sales promotion of a product or a service is provided. An information providing site is provided with a simple diagnosis processing portion for performing a simple skin diagnosis of a user of a terminal device, a simple result transmitting portion for transmitting simple diagnosis data and an ID key to the user, and a customer data extracting portion for transmitting private data and the simple diagnosis data to a service providing site. The service providing site is provided with an ID key receiving portion for receiving the ID key from the user, a customer data requesting portion for transmitting the ID key to the information providing site, and a customer data receiving portion for receiving private data corresponding to the ID key. The customer data extracting portion transmits private data corresponding to the ID key transmitted by the customer data requesting portion.

12 Claims, 16 Drawing Sheets

Fig. 7

URL http://www.xxxA.com/cosmecheck.html

WELCOME! CHECK YOUR SKIN ON WEB PAGE.
ANSWER A QUESTIONNAIRE. RESULT IS SENT VIA E-MAIL.

Q1. AVERAGE SLEEP TIME?
☐ SIX HOURS OR LESS  ☐ SEVEN HOURS  ← CB4
☐ EIGHT HOURS OR MORE
Q2. MAKE-UP TIME?
☐ TEN MINUTES OR LESS  ☐ THIRTY MINUTES  ← CB4
☐ ONE HOUR OR MORE
Q3. YOUR SKIN IS···
☐ XXX TYPE  ☐ YYY TYPE  ☐ ZZZ TYPE  ← CB4

⋮

Qn. PLEASE ANSWER THE FOLLOWING ITEMS FOR
CHECKING IN MORE DETAIL.
NAME: (MUST) [_____] ~TX4
SEX: (MUST) [_____] ~TX4
ADDRESS: [_____] ~TX4
BIRTHDAY: [_____] ~TX4
AGE: (MUST) [_____] ~TX4
OCCUPATION: [_____] ~TX4
ELECTRONIC MAIL ADDRESS: (MUST) [_____]
　　　　　　　　　　　　　　　　　　　TX4　ARD

[ SEND ]  [ CANCEL ]

SENDER: Woman@◯◯◯REPRESENTATIVE
DATE AND TIME: DECEMBER 30, 2000
TO: ◯◯◯ △△△
SUBJECT: SKIN DIAGNOSIS RESULT DEAR ◯◯◯ △△△,
   THANK YOU FOR YOUR ANSWERS IN SKIN DIAGNOSIS CHECK.
   DIAGNOSIS RESULT CAN BE SEEN IN THE FOLLOWING URL.
   http://www.xxxxA.com/zzzz/zzzz/AB123/ ⟵ 2Lm 2m1

Fig. 9

URL http://www.xxxxA.com/zzzz/zzzz/AB123/

DEAR ○○○ △△△,
　THANK YOU FOR YOUR USE.
　YOUR SKIN DIAGNOSIS RESULT IS

○×△□ ○×△□ ○×△□ ○×△□
○×△□ ○×△□ ○×△□ ○×△□
○×△□ ○×△□ ○×△□.

WILL YOU CHECK IN MORE DETAIL
BY USING DIAGNOSIS KIT?
THIS CHECK COSTS TO YOU.
LINK TO COOPERATION SITES AFTER THE CHECK,
SO PAYBACK SERVICE IS AVAILABLE!
DIAGNOSIS KIT WILL BE MAILED TO YOU.
PLEASE FILL OUT NAME AND ADDRESS CORRECTLY.

NAME: [　　　　　　　]—TX5

ADDRESS: [　　　　　　　]—TX5

—BN5
[　REQUEST　]　　[　NOT REQUEST　]

SENDER: Woman@○○○REPRESENTATIVE
DATE AND TIME: DECEMBER 30, 2000
TO: ○○ ○○
SUBJECT: DIAGNOSIS KIT CHECK RESULT

DEAR ○○ ○○,

THANK YOU FOR USING DIAGNOSIS KIT CHECK. DIAGNOSIS RESULT CAN BE SEEN IN THE FOLLOWING URL.
http://www.xxxxA.com/zzzz/zzzz/AB123/ — 2Ln 2m2

COMMUNICATION SYSTEM, INFORMATION AGENT METHOD AND RECORDING MEDIUM

BACKGROUND OF THE INVENTION

1. Field of the Invention

The present invention is related to a communication system, an information agent method and a recording medium for providing a product or a service at a site on the Internet.

2. Description of the Prior Art

Conventionally, a method of distributing a free sample of a product or a service to a potential customer has been widely used for promoting the sales. A research card may be attached to the sample. A provider may analyze a result of the research statistically about tastes of customers and utilize the result for developing a new product or service. The provider can also perform a test for each customer and propose a product or a service suitable for the customer. In addition, the provider may send a direct mail to the customer at the address written in the research card for sales promotion.

For example, a cosmetician company may distribute a sample of their cosmetic products at a place such as a shopping center or send the sample to customer's addresses. Customers who received the sample may try the sample, answer the questions in a research card attached to the sample and send the research card back to the cosmetician company. The cosmetician company may propose a suitable product to the customer in accordance with the research card.

However, unselective distribution of the sample to customers can cause a large amount of waste in labor costs, portage costs, communication costs, and the samples. Recently, many kinds of products or services whose target customers are narrowed have been designed. Therefore, it is important to select potential customers to be distributed a sample.

There is a method of opening a web page at a site on the Internet for transmitting information about products or services and to send samples to users who have got access to the web page.

Such users who have got access to the web page likely have an interest in the company or their products or services, so there is high possibility that the users purchase a product or a service of the company. Namely, in order to distribute a sample efficiently, it may effective to narrow the target to the users who have got access to the web page.

However, there are many web pages that transmit information about products or services on the Internet. Therefore, the number of accesses to the web page by users who have appetite for buying a product or a service is usually smaller than the number the provider expects.

Moreover, even if the user gets access to the Web site, it is possible that the user does not teach his or her name and address to the provider because such private information can leak from the web page or can be used for undesired invitation. In this case, the provider cannot send a sample to the user.

Therefore, by this method, sufficient effect of sales promotion cannot be expected.

SUMMARY OF THE INVENTION

The object of the present invention is to provide a communication system, an information agent method and a recording medium for performing sales promotion effectively to customers so that the customers can receive a product or services from a provider securely.

The communication system according to one embodiment of the present invention is a communication system for communicating information between sites that are connected to each other via a network. The communication system comprises a first site and a second site. The first site includes diagnosis means for performing a diagnosis of a user of a terminal device on the network, memory means for memorizing private information of the user and a diagnosis result of the diagnosis means together with an ID key, first transmission means for transmitting the diagnosis result and the ID key to the user, and second transmission means for transmitting the private information and the diagnosis result to the second site. The second site includes ID key reception means for receiving the ID key from the user, ID key transmission means for transmitting the ID key received by the ID key reception means to the first site, and user information reception means for receiving the private information corresponding to the ID key transmitted to the first site and the diagnosis result from the first site. The second transmission means transmit the private information corresponding to the ID key indicated by the second site and the diagnosis result.

In another embodiment of the communication system, the first site includes memory means for memorizing private information of the user of a terminal device on the network together with an ID key, first transmission means for transmitting the ID key to the user, and second transmission means for transmitting the private information to a second site. The second site includes result transmission means for transmitting a result of a diagnosis performed for the user to the first site, ID key reception means for receiving the ID key from the user, ID key transmission means for transmitting the ID key received by the ID key reception means to the first site, and user information reception means for receiving the private information corresponding to the ID key transmitted to the first site from the first site. The memory means memorize the diagnosis result received from the second site together with the ID key, and the first transmission means transmit the diagnosis result corresponding to the ID key.

Preferably, the ID key includes disclosable information concerning items of the private information that can be disclosed to the second site, and the second transmission means transmit only items of the private information corresponding to the disclosable information.

In another aspect of the present invention, the communication system comprises a first site for giving information to a user of a terminal device that can be connected to a network and a second site for giving information to the user for providing the product or the service. The first site includes diagnosis means for performing a diagnosis of the user for providing a product or a service, memory means for memorizing private information of the user and a diagnosis result of the diagnosis means together with an ID key, first transmission means for transmitting the diagnosis result and the ID key to the user, and second transmission means for transmitting the private information and the diagnosis result to the second site. The second site includes ID key reception means for receiving the ID key from the user, ID key transmission means for transmitting the ID key received by the ID key reception means to the first site, and user information reception means for receiving the private information corresponding to the ID key transmitted to the first site and the diagnosis result from the first site. The ID key includes disclosable information concerning items of the private information that can be disclosed to the second site, and the second transmission means transmit only items of the private information corresponding to the disclosable information of the ID key indicated by the second site.

A server according to one embodiment of the present invention is a server that is used for the information providing site for giving information to a user of a terminal device that can be connected to a network. The server comprises diagnosis means for performing diagnosis of the user, memory means for memorizing private information of the user and a diagnosis result of the diagnosis means together with an ID key, first transmission means for transmitting the diagnosis result and the ID key to the user, and second transmission means for transmitting the private information and the diagnosis result to another site. The ID key includes disclosable information concerning items of the private information that can be disclosed to the other site, and the second transmission means transmit only items of the private information corresponding to the disclosable information.

A method according to one embodiment of the present invention is an information agent method for mediating information between a consumer of a product or a service and a provider who provides the product or the service to the consumer using a computer and a network. The method comprises the steps of memorizing private information of the consumer, acquiring a result of a diagnosis of the consumer for providing the product or service, issuing an ID key for linking the result information and the private information, giving the diagnosis result and the ID key to the consumer, and transmitting the private information corresponding to the ID key to the provider when the ID key obtained from the consumer is disclosed by the provider.

In another embodiment of the information agent method, the method comprising the steps of passing an article received from the consumer after being used for a diagnosis for providing the product or the service to the provider, obtaining a result of the diagnosis, memorizing private information of the consumer together with an ID key, transmitting the diagnosis result and the ID key to the consumer, and transmitting the private information corresponding to the ID key indicated by the provider to the provider.

In another embodiment of the communication system, the first site includes memory means for memorizing private information of a user of a terminal device on the network and a result of a diagnosis of the user together with an ID key, first transmission means for transmitting the diagnosis result and the ID key to the user, and second transmission means for transmitting the private information to a second site. The second site includes ID key reception means for receiving the ID key from the user, ID key transmission means for transmitting the ID key received by the ID key reception means to the first site, and user information reception means for receiving the private information corresponding to the ID key transmitted to the first site from the first site. The first transmission means transmit the diagnosis result corresponding to the ID key.

A recording medium according to one embodiment of the present invention is a recording medium that can be read by a computer for a server used for an information providing site that gives information to a user of a terminal device that can be connected to a network. The recording medium stores a program for making the computer execute the processes including a diagnosis process of performing a diagnosis of the user, a memorizing process of memorizing private information of the user and a diagnosis result of the diagnosis process together with an ID key, a first transmission process of transmitting the diagnosis result and the ID key to the user, and a second transmission process of transmitting the private information designated by the ID key and the diagnosis result to another site.

The communication system or the server according to the present invention is realized by using a personal computer or a workstation. The program for realizing the method according to the present invention is stored in a recording medium such as a semiconductor memory, a hard disk, a CD-ROM, a floppy disk or a magneto optical disk. The program stored in the recording medium is loaded into a main memory and executed by a processor. On this occasion, a CD-ROM drive, a floppy disk drive or a magneto optical disk drive is used as required. If the recording medium is provided in a server that is connected via a communication line such as a network, the program is read or downloaded from the server via the communication line. If the program is transferred to the processor via the communication line, the communication line also corresponds to the recording medium. The program can be supplied in a form of working on various types of operating systems and platforms, or under various system or network environments. The language "diagnosis" in this specification means, for example, asking a user to answer questions, analyzing the answers statistically, providing the user a sample, and analyzing a result of use of the sample statistically.

BRIEF DESCRIPTION OF THE DRAWINGS

FIG. 7 shows an example of a web page for the simple skin diagnosis.

FIG. 8 shows an example of an electronic mail concerning a result of the simple skin diagnosis.

FIG. 9 shows an example of a web page showing a result of the simple skin diagnosis.

FIG. 10 shows an example of an electronic mail concerning a result of a detail skin diagnosis.

DESCRIPTION OF THE PREFERRED EMBODIMENTS

Hereinafter, the present invention will be explained more in detail with reference to embodiments and drawings.

Figure 1:
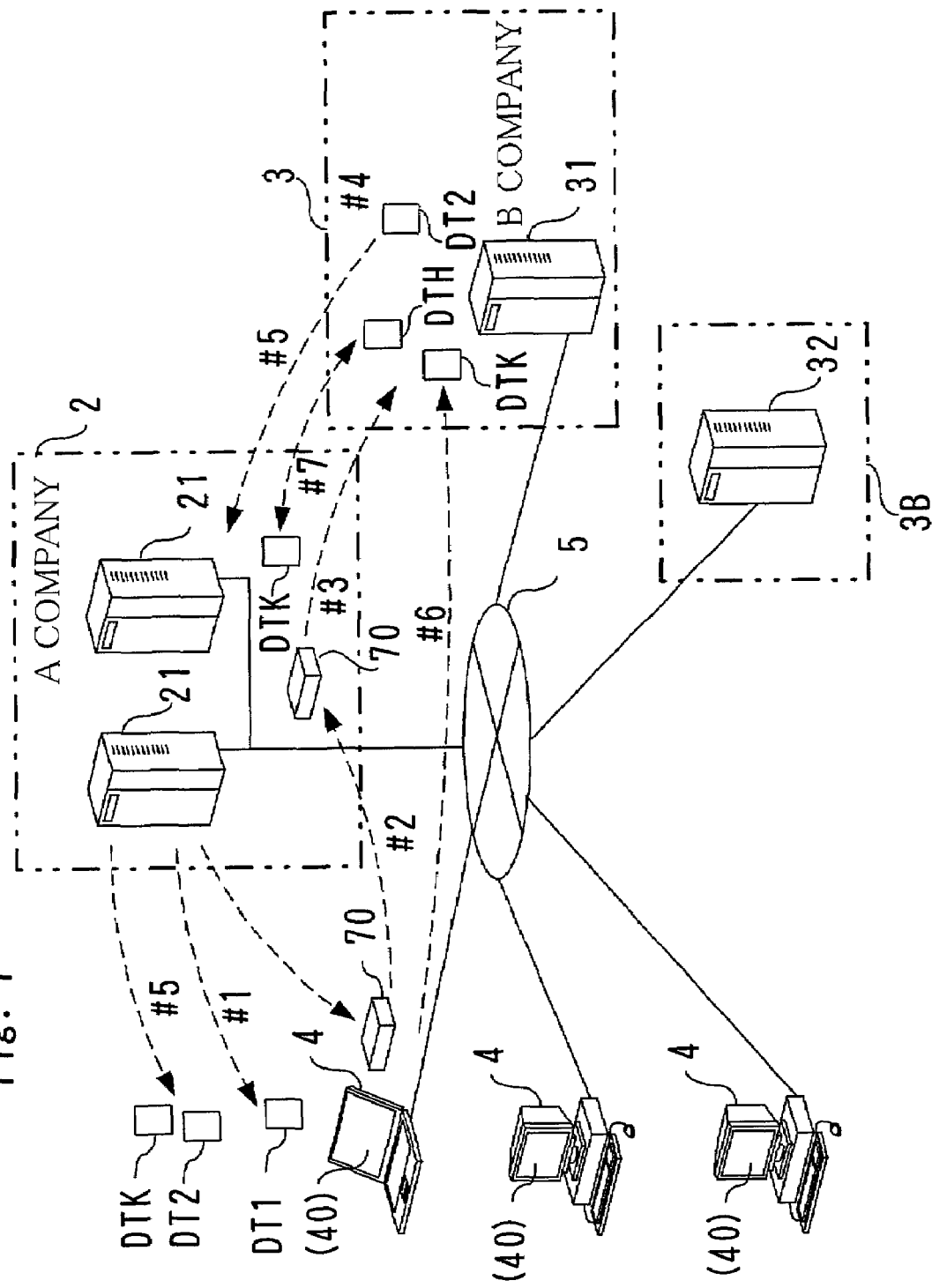
FIG. 1 shows an example of structure of a communication system according to the present invention.

As shown in FIG. 1, a communication system 1 comprises an information providing site 2, a service providing site 3, a terminal device 4, and a communication line 5.

The information providing site 2 is administered by an Internet service provider, an Internet search service company or other companies. Users on the Internet can acquire or search various kinds of information via the information providing site 2.

Figure 4:
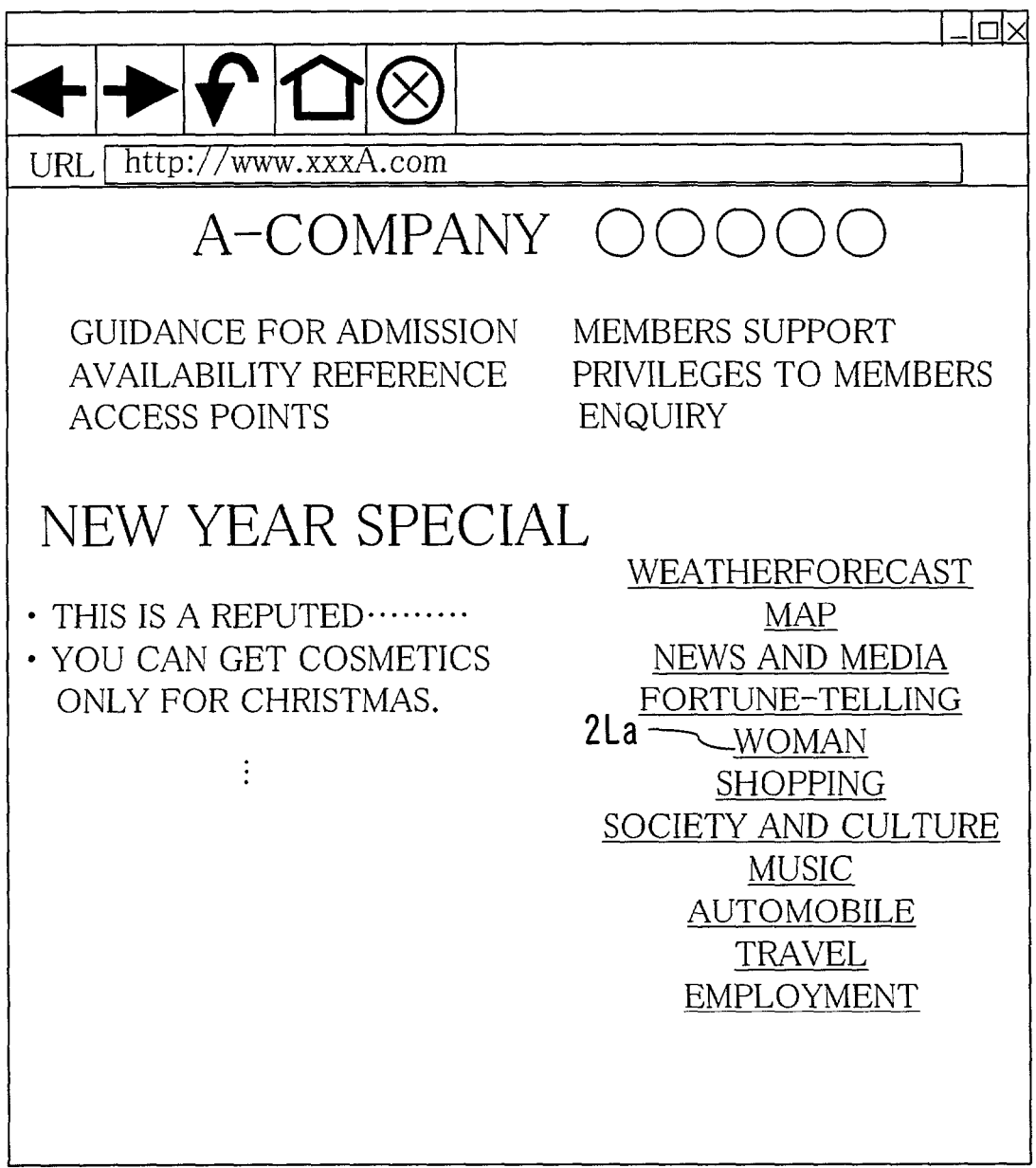
FIG. 4 shows an example of a web page used as a top page of the information providing site.
Figure 5:
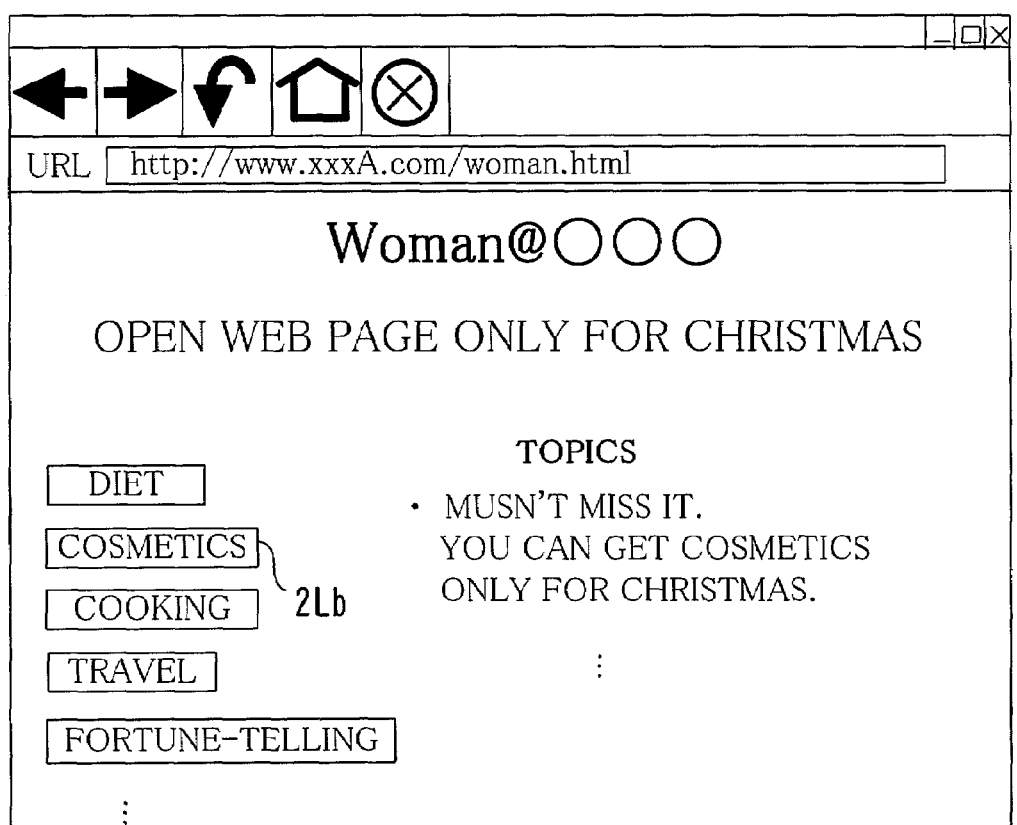
FIGS. 5 and 6 show examples of a web page having a link to a simple skin diagnosis.
Figure 6:
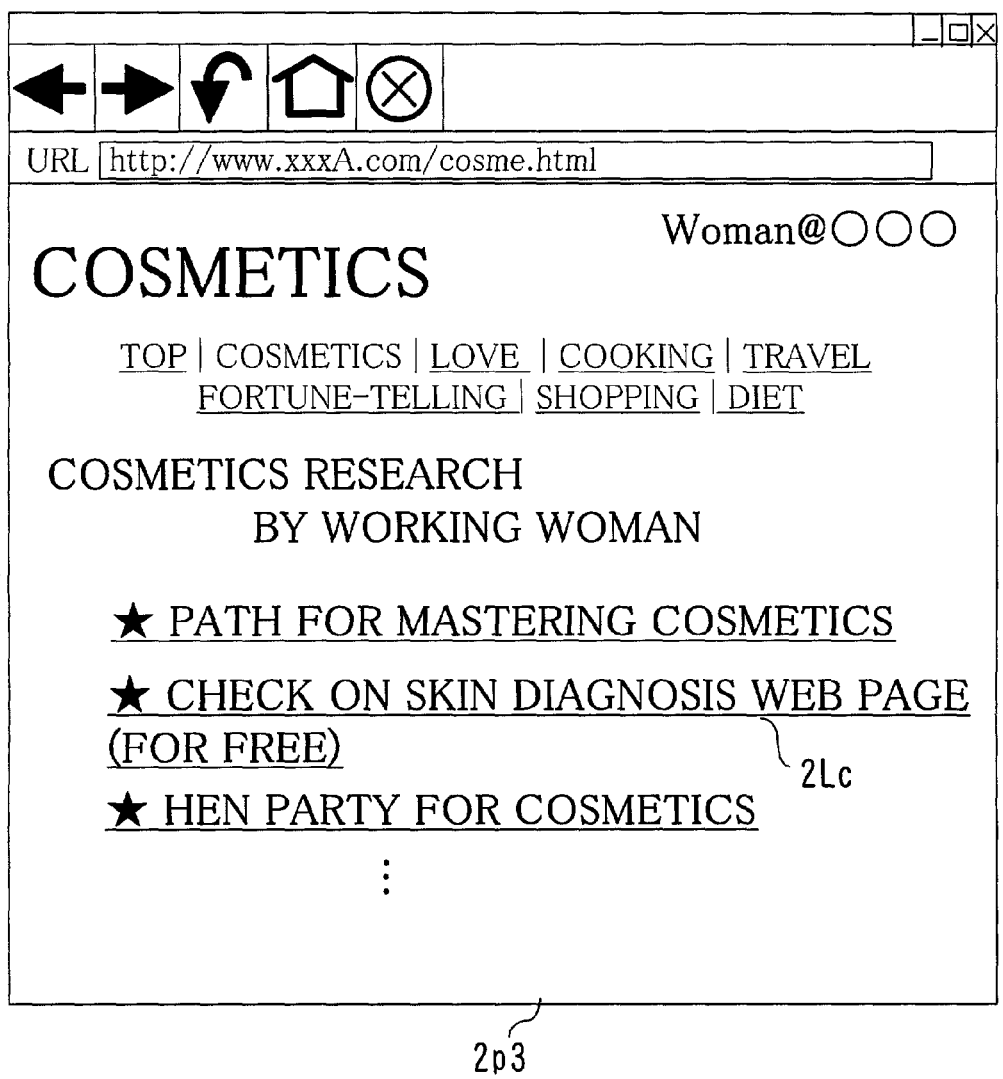

In an example of this embodiment, the information providing site 2 is administered by an Internet service provider "A-Company" that provides various kinds of information concerning news, fortune—telling, trips or others. As information providing means, web pages $2p1$–$2p3$ shown in FIGS. 4–6 are used, for example. A user can get access to the web pages $2p1$–$2p3$ using a WWW browser. The A-Company also provides connection service to the Internet for the terminal device 4 and has individual information or data of many members.

The service providing site 3 is administered by a group of companies that provides products or services or by a third party under a commission from the group.

In an example of this embodiment, the service providing site 3 is administered by "B-Company" that provides cosmetics. The B-Company displays information about the company's products on the web page of the service providing site 3. A user on the Internet can obtain information concerning a product or a service of the company via the service providing site 3.

The B-Company performs a skin diagnosis of a user that is a consumer before the user purchases a product, as an event of sales promotion. The event of the skin diagnosis includes two types. In one type, a web page $2p4$ for the skin diagnosis as shown in FIG. 7 is provided at the information providing site 2, and the skin diagnosis is performed in accordance with the user's answer to questions on the web page $2p4$. Hereinafter, this skin diagnosis is referred to as a "simple skin diagnosis."

In another type of skin diagnosis, a diagnosis kit 70 is sent to a user, and the skin diagnosis is performed by analyzing the diagnosis kit 70 that was returned from the user. For example, the diagnosis kit 70 includes a film or a test paper for extracting fat in the skin or for measuring moisture content in the skin. The user uses the diagnosis kit 70 and sends back the diagnosis kit 70 that has extracted fat in the skin, for example. A-Company acts as an agent for B-Company concerning the transmission and recovery of the diagnosis kit 70. Hereinafter, this skin diagnosis is referred to as a "detail skin diagnosis."

In this way, since the simple skin diagnosis and the detail skin diagnosis are performed by the B-Company indirectly via A-Company, private information such as a name or an address of the user is disclosed only to the A-Company and is not disclosed to the B-Company. The user has a contract with the A-Company as a service provider and there is a certain trust between the user and the A-Company. Therefore, the user may not hesitate to let the private information be known by the A-Company, so as to get access to the information providing site 2 of the A-Company easily for the skin diagnosis. The B-Company can get many users who utilize the sales promotion event via the A-Company. The simple skin diagnosis is performed at no charge, and the detail skin diagnosis is performed at cost to the user. However, under a predetermined condition, a fee of the detail skin diagnosis is paid back partially or entirely.

Before explaining the structures and functions of the information providing site 2 and others, a general flow from the simple skin diagnosis and the detail skin diagnosis to provision of products from the B-Company to the user will be explained with reference to a flowchart.

Figure 2:
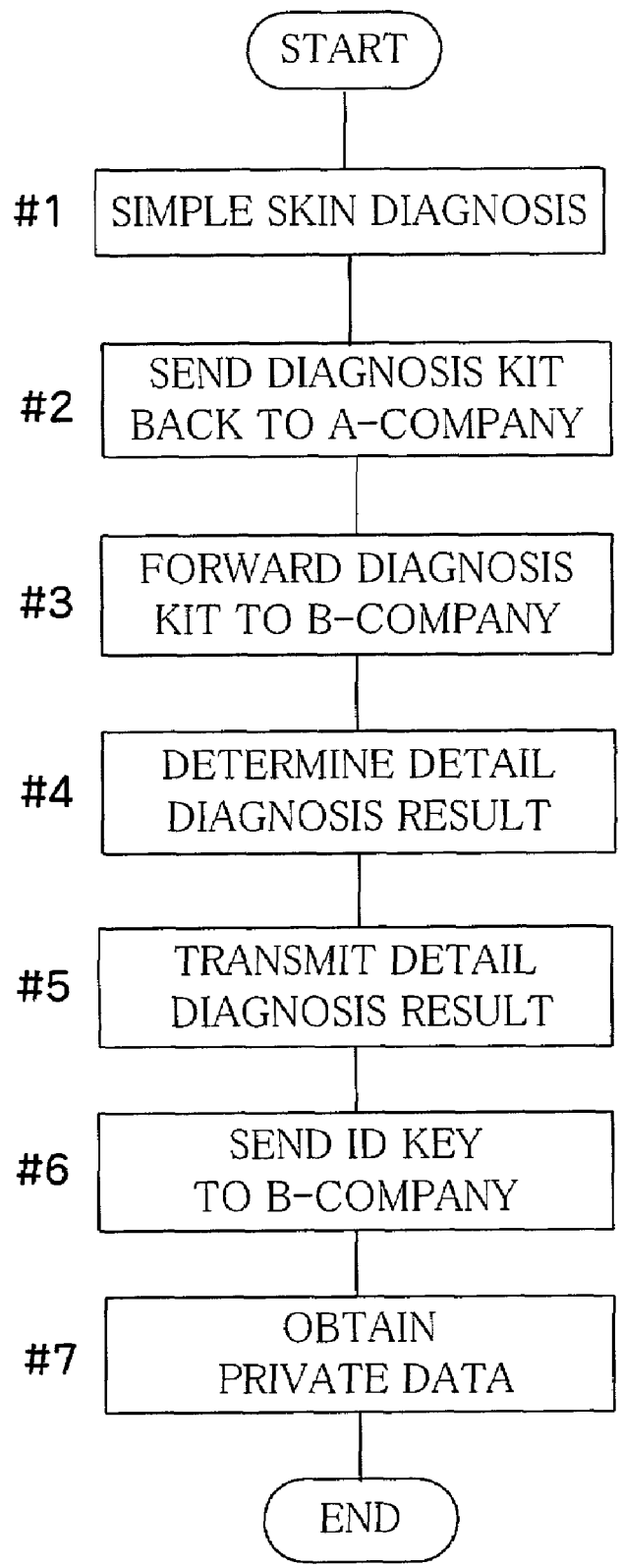
FIG. 2 is a flowchart of a process in an embodiment of the present invention.

As shown in FIG. 2, the user uses the terminal device 4 to get access to the web page $2p4$ of the information providing site 2 for performing the simple skin diagnosis and obtaining data about the diagnosis result (Step #1). Hereinafter, such data are referred to as "simple diagnosis result DT1."

If the user desires a detail skin diagnosis after seeing the result of the simple skin diagnosis, the user applies to the A-Company and receives the diagnosis kit 70 for the detail skin diagnosis from the A-Company. After extracting fat in the skin by using the diagnosis kit 70, the user send the diagnosis kit 70 back to the A-Company (Step #2).

The A-Company passes the received diagnosis kit 70 to the B-Company after hiding private data of the user such as a name or an address (Step #3). The B-Company analyzes the diagnosis kit 70 that was received from the A-Company, so as to determine data concerning the diagnosis result (Step #4). Hereinafter, private data concerning the user is referred to as "private data DTH", while data concerning the diagnosis result of Step # 4 is referred to as "detail diagnosis result DT2".

The detail diagnosis result DT2 is transmitted to the user via the A-Company. On this occasion, the A-Company issues an ID key DTK to the user for identifying the user. The detail diagnosis result DT2 is transmitted to the user together with the ID key DTK (Step #5). If the user wishes to buy a product or a service of the B-Company by permitting the B-Company to know the private data DTH after checking the result of the detail skin diagnosis, the user gets access to the service providing site 3 and sends the ID key DTK to the B-Company (Step #6).

The B-Company can use the ID key DTK that was sent from the user so as to obtain the private data DTH of the user from the information providing site 2 (Step #7). After that, the B-Company can use the private data DTH for providing a product or a service that is the most suitable for the user.

In other words, the user (consumer) who is expected to have a desire to buy is found by the simple skin diagnosis, and a product that is suitable for the user is proposed and provided to the user by the detail skin diagnosis.

Referring to FIG. 1 again, the information providing site 2 is realized by hardware including a server 21 and network equipment and various software. The server 21 comprises a CPU, a RAM, a ROM, a communication control device, and a magnetic disk drive. The server 21 can be connected to an external magneto optical disk drive or a CD-ROM drive.

Figure 16:
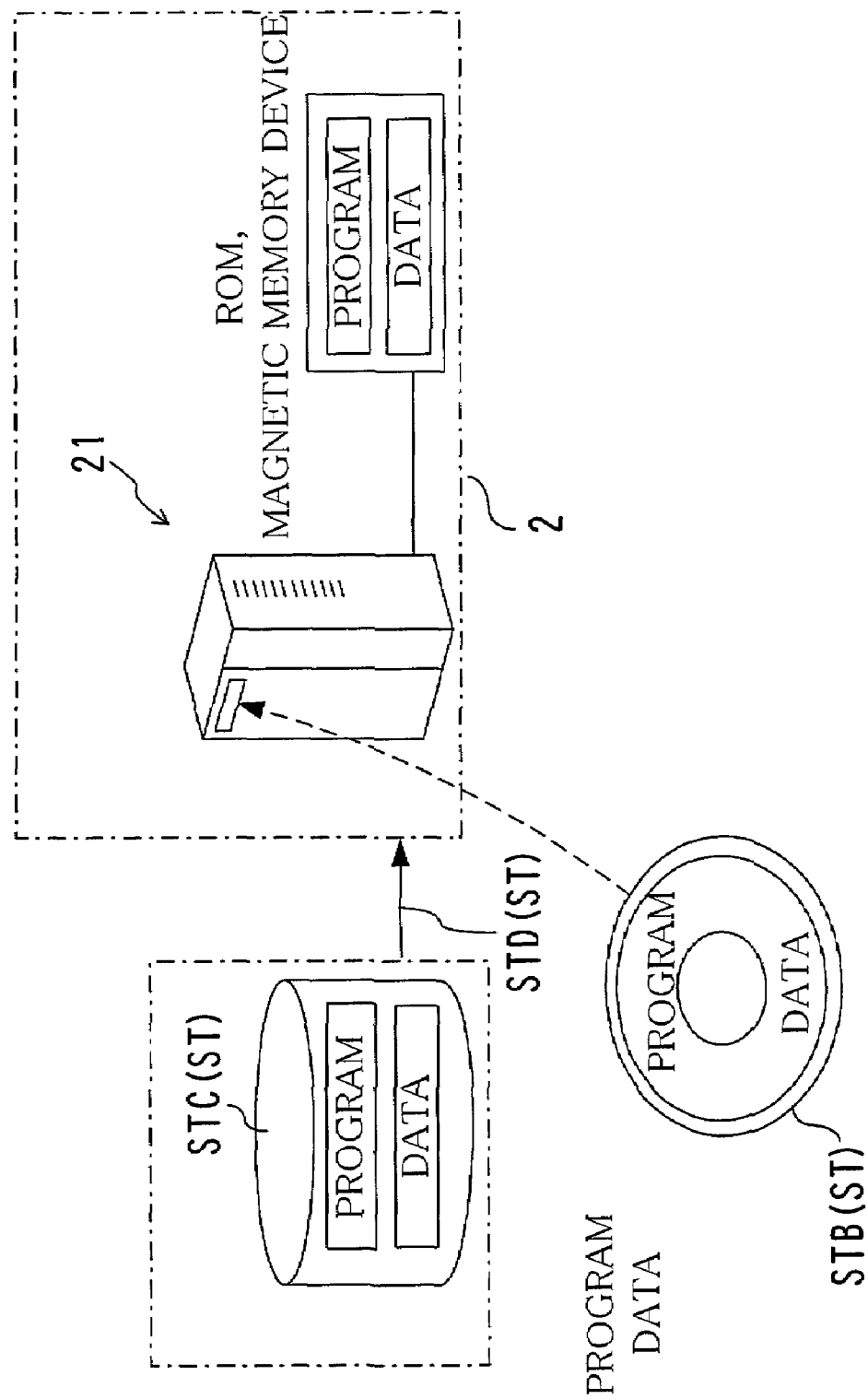
FIG. 16 is a diagram showing a form of a recording medium storing a program for executing a method of the present invention.

The ROM or the magnetic disk drive stores an operating system, a software program for executing a process that will be explained later and data. The program can be supplied in a form that the program works on various operating systems and platforms, or under various system environment and network environment. The program and data are loaded into the RAM and are executed by the CPU. The program and data can be loaded from another recording medium ST. For example, as shown in FIG. 16, a portable medium STB such as a CD-ROM, a floppy disk, or a magneto optical disk, network, or a network medium STC such as a server or a DASD that is connected via a communication line STD, or the communication line STD itself can be used as the recording medium ST. If the recording medium ST is a portable medium STB, the program is read out by a drive corresponding to a type of the portable medium STB, stored in a magnetic memory device of the server 21, or loaded into the memory for being executed. If the recording medium ST is the network medium STC, the program is downloaded via the communication line STD into the magnetic memory device, or loaded into the memory for being executed.

The service providing site 3 is realized by hardware such as a server 31 and network equipment and various software in the same way as the information providing site 2.

The terminal device 4 comprises a CPU, a RAM, a communication control device, a memory device such as a magnetic disk drive or a ROM, and a display device. The memory device memories a WWW browser 40. The WWW browser 40 is used for obtaining various information from the web page of the information providing site 2 or the service providing site 3. The obtained information is displayed on the display screen of the display device. The terminal device 4 includes a personal computer, a workstation, a cellular phone or a microcellular phone.

The server 21 or 31 and the terminal device 4 are connected to each other via the communication line 5. The communication line 5 includes the Internet, an intranet, a private line, or a public telephone line. Among these devices, communication protocols such as TCP/IP, HTTP, SMTP, POP3, IMAP, and FTP are used.

Figure 3:
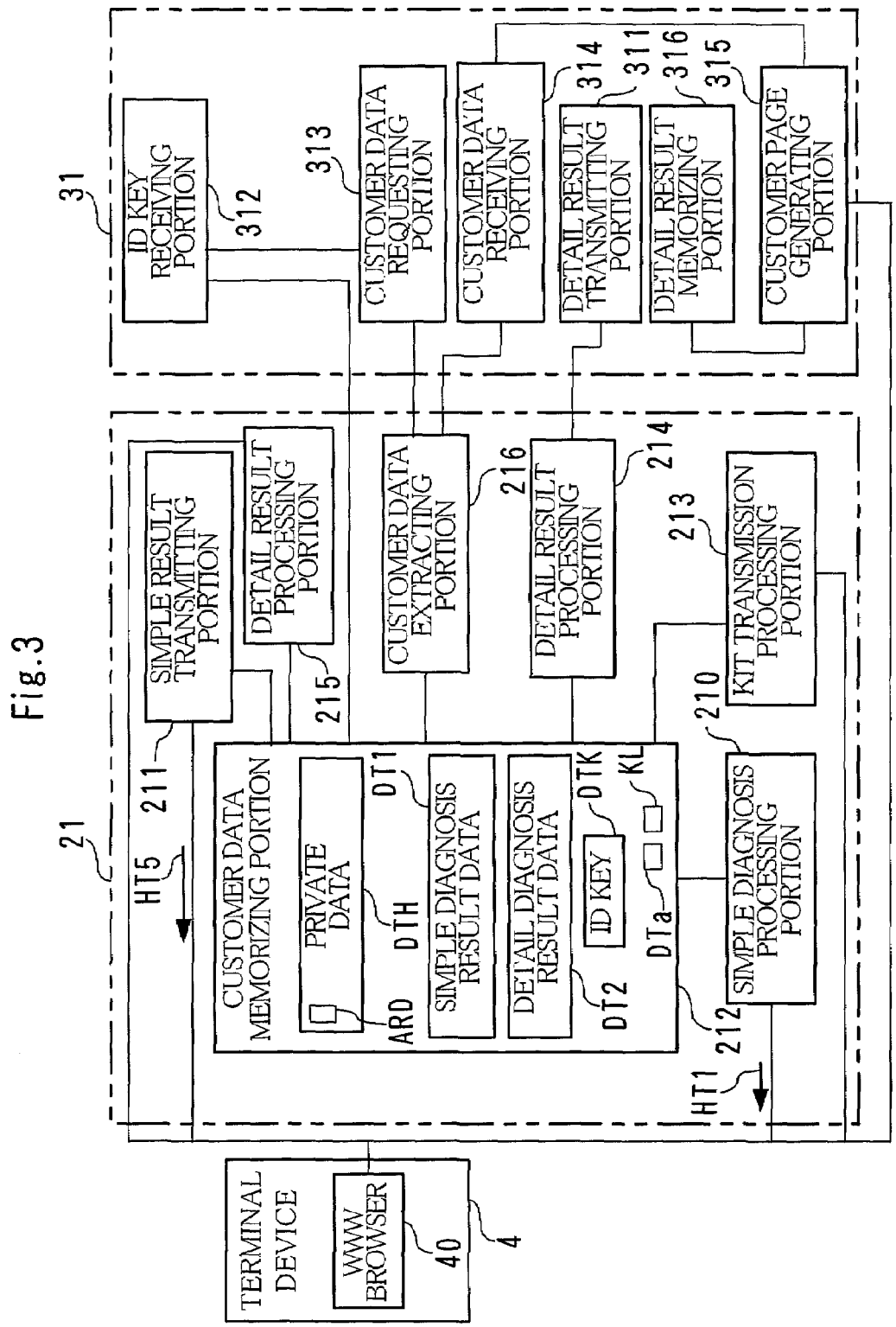
FIG. 3 shows functional structures of an information providing site and a service providing site.

By this structure, the server 21 of the information providing site comprises, as shown in FIG. 3, functional portions such as an simple diagnosis processing portion 210, an simple result transmitting portion 211, a customer data memorizing portion 212, a kit transmission processing portion 213, a detail result processing portion 214, a detail result transmitting portion 215, and a customer data extracting portion 216. Furthermore, the server 31 of the service providing site comprises functional portions such as a detail result transmitting portion 311, an ID key receiving portion 312, a customer data requesting portion 313, a customer data receiving portion 314, a customer page generating portion 315, and a detail result memorizing portion 316.

The simple diagnosis processing portion 210 performs a process concerning the simple skin diagnosis as follows.

First, the simple diagnosis processing portion 210 transmits a hypertext HT1 and necessary image files for displaying the web page 2p4 shown in FIG. 7 to the terminal device 4. The web page 2p4 contains check boxes CB4 for answering to questions about sleep time or make-up time necessary for the simple skin diagnosis and text boxes TX4 for inputting user's name, sex, address, age, occupation or electronic mail address. Answers to such questions are inputted at the terminal device 4. On this occasion, the user has to answer correctly to questions necessary for the skin diagnosis but is not required to answer to questions that are not relevant to the skin diagnosis. For example, a nickname can be used instead of the user's name. The address or the occupation is not required to be inputted. However, since the electronic mail address is used as an address of transmission of the electronic mail 2m1 shown in FIG. 8, it has to be inputted correctly.

After the answers are obtained from the terminal device 4, a predetermined operational process is performed in accordance with a preset program, so that the simple diagnosis result DT1 is generated. A diagnosis code DTa for identifying each simple diagnosis result DT1 is issued, and the simple diagnosis result DT1 as well as the diagnosis code DTa is memorized in the customer data memorizing portion 212. For example, a character string such as "AB123" is used as the diagnosis code DTa. Then, the electronic mail 2m1 shown in FIG. 8 is generated and is transmitted to the electronic mail address of the user. A structure of the electronic mail 2m1 will be explained later. The answer that has obtained from the terminal device 4 can be also memorized in the customer data memorizing portion 212. This answer can be used for another diagnosis.

In general, the top page of the information providing site of the Internet service provider is usually used as a portal site of the WWW browser. In order to increase the number of accesses to the web page 2p4, the web pages 2p1–2p3 are designed so that the web page 2p4 can be accessed by tracing hyperlinks from the web page 2p1 that is the top page of the information providing site 2, as shown in FIGS. 4–6.

The web page 2p1 contains the hyperlink 2La to the web page 2p2. In the same manner, the web page 2p2 contains the hyperlink 2Lb to the web page 2p3, and the web page 2p3 contains the hyperlink 2Lc to the web page 2p4. The user can reach the web page 2p4 easily by clicking the hyperlinks 2La and 2Lb in order. It is possible to get access to the web page 2p4 by designating the URL of the web page 2p4 in the WWW browser 40.

Referring to FIG. 3 again, the simple result transmitting portion 211 generates a hypertext HT5 for displaying a web page 2p5 shown in FIG. 9 in accordance with the simple diagnosis result DT1 and transmits the hypertext HT5 to the terminal device 4 as follows.

As shown in FIG. 8, the electronic mail 2m1 is provided with a hyperlink 2Lm that indicates the URL of the web page 2p5. The string "AB123" in the URL corresponds to the diagnosis code DTa. Therefore, when the hyperlink 2Lm is clicked by the terminal device 4, the simple result transmitting portion 211 extracts the simple diagnosis result DT1 corresponding to the diagnosis code DTa that is indicated by the string "AB123" in the URL out of the customer data memorizing portion 212. Then, the simple result transmitting portion 211 generates the hypertext HT5, which is transmitted to the terminal device 4.

The web page 2p5 contains the diagnosis result of the simple skin diagnosis, an explanation text for inviting the detail skin diagnosis and a text box TX5 for inputting an address to which the diagnosis kit 70 for the detail skin diagnosis is transmitted, as shown in FIG. 9.

The kit transmission processing portion 213 receives a request for sending of the diagnosis kit 70 from the terminal device 4 that has got access to the web page 2p5 and memorizes the private data DTH of the user into the customer data memorizing portion 212. Namely, when a button BN5 of the web page 2p5 shown FIG. 9 is clicked in the terminal device 4, the kit transmission processing portion 213 acquires the name and the address that were inputted in the text box TX5 of the web page 2p5 from the terminal device 4. Then, in relationship with the diagnosis code DTa, the acquired data are memorized as the private data DTH into the customer data memorizing portion 212.

After the process of the kit transmission processing portion 213, the A-Company sends the diagnosis kit 70 to the user by means of mail or a home-delivery service. After receiving the diagnosis kit 70, the user uses the diagnosis kit 70 for the test and sends back the used diagnosis kit 70 to the A-Company. Then, the A-Company passes the diagnosis kit 70 to the B-Company attached to the diagnosis code DTa instead of the name of the user.

The B-Company generates the detail diagnosis result DT2 by analyzing the diagnosis kit 70. Then, the detail result transmitting portion 311 of the service providing site 3 transmits the generated detail diagnosis result DT2 to the information providing site 2 together with the diagnosis code DTa. The detail diagnosis result DT2 is memorized into the detail result memorizing portion 316.

Figure 11:
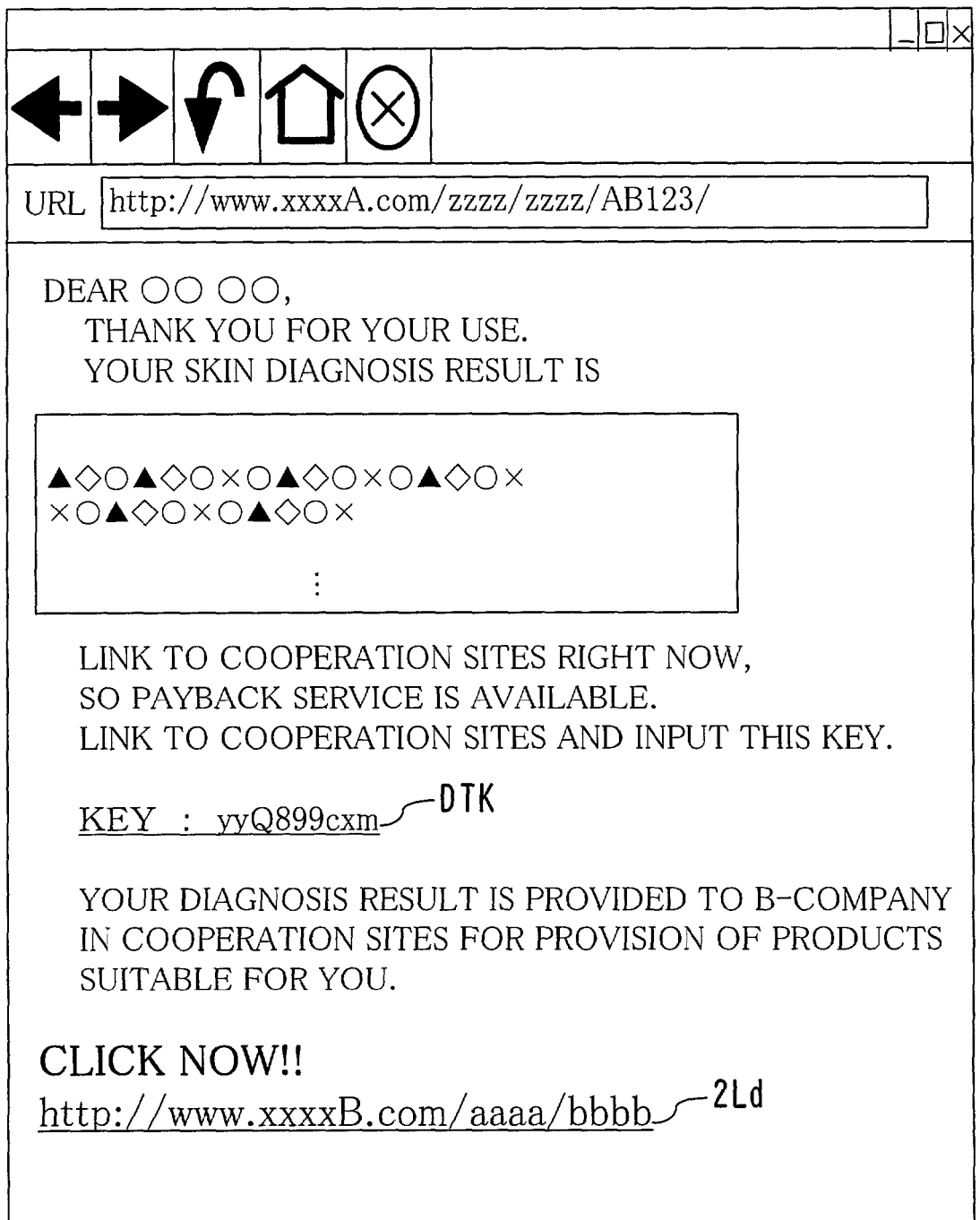
FIG. 11 shows an example of a web page showing a result of the detail skin diagnosis.

The detail result processing portion 214 receives the detail diagnosis result DT2 from the detail result transmitting portion 311 and issues the ID key DTK. The detail diagnosis result DT2 and the ID key DTK are memorized into the customer data memorizing portion 212 in relationship with the diagnosis code DTa. Then, the detail result processing portion 214 generates the electronic mail $2m2$ that is shown in FIG. 10 and transmits the electronic mail $2m2$ to the terminal device 4. The electronic mail $2m2$ is provided with the hyperlink 2Ln that indicates the URL of the web page $2p6$ shown in FIG. 11.

The detail result transmitting portion 215 generates the hypertext HT6 for displaying the web page $2p6$ in accordance with the detail diagnosis result DT2 and the ID key DTK and transmits the hypertext HT6 to the terminal device 4. The method of the above-mentioned process is substantially the same as that in the simple result transmitting portion 211. The web page $2p6$ contains the diagnosis result of the detail skin diagnosis, the ID key DTK and the hyperlink 2Ld to the service providing site 3.

Figure 12:
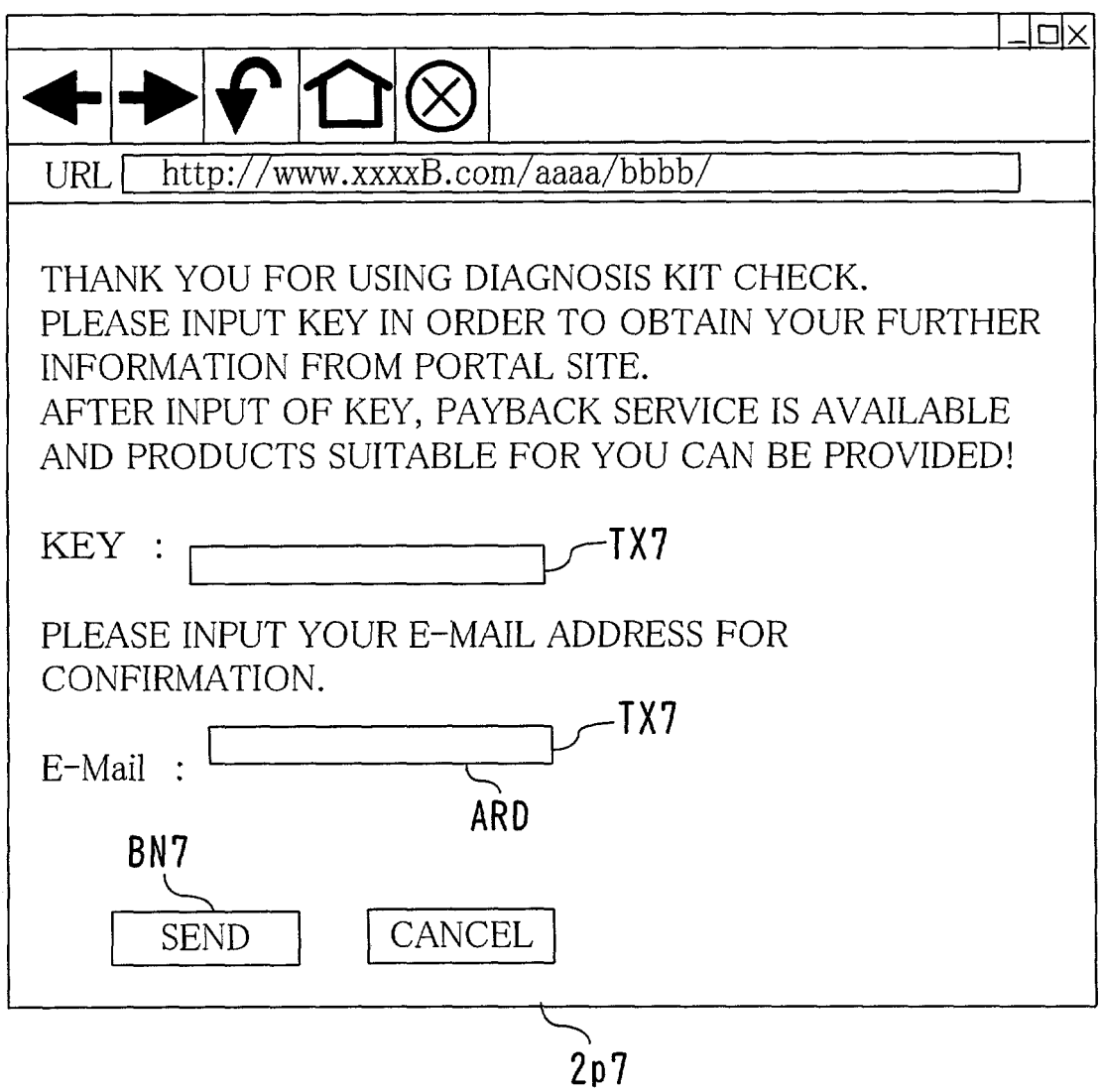
FIG. 12 shows an example of a web page for inputting an ID key.
Figure 14:
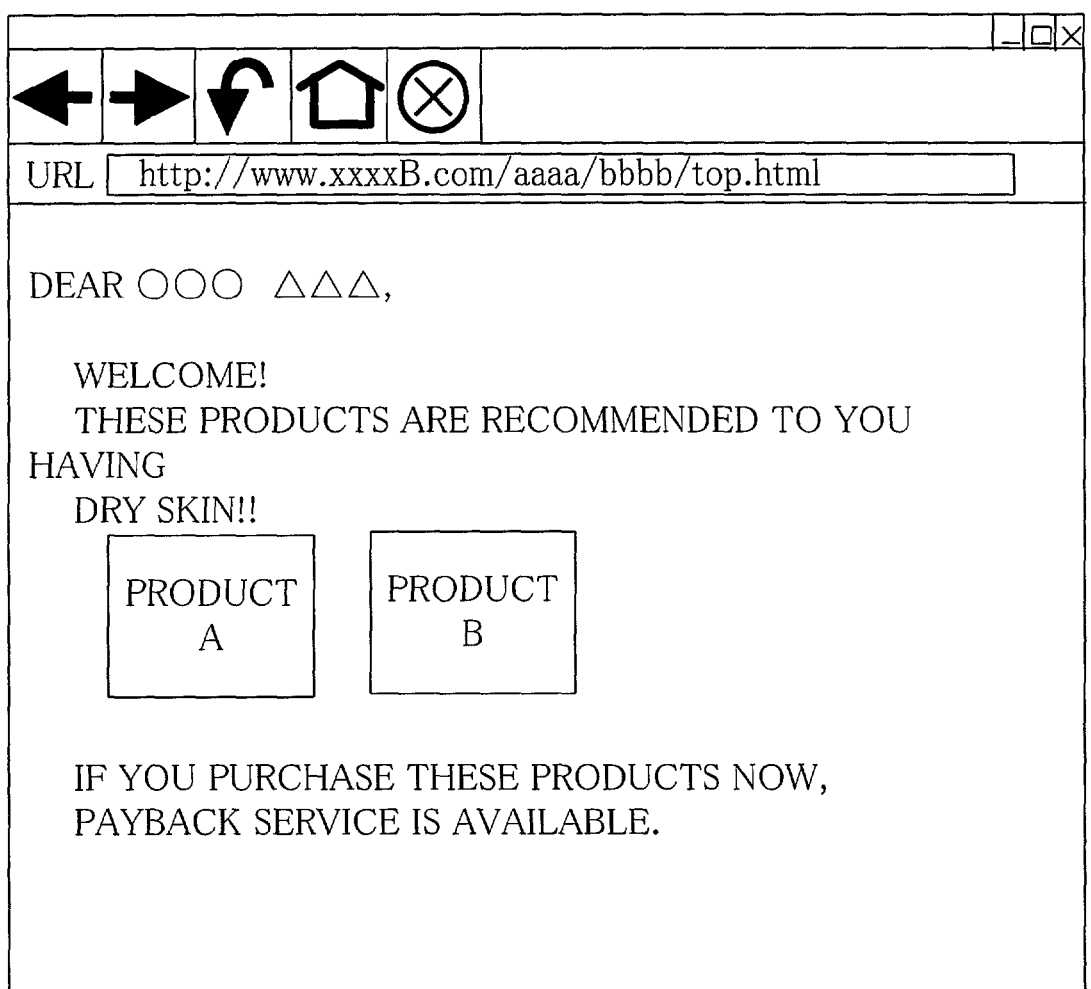
FIG. 14 shows an example of a web page that is customized for each user.

When the hyperlink 2Ld in the web page $2p6$ is clicked in the terminal device 4 that has received the hypertext HT6, the access to the web page $2p7$ shown in FIG. 12 is performed. The received ID key DTK and the electronic mail address ARD of the user are inputted in the text box TX7 of the web page $2p7$ and a button BN7 is clicked. Then the access to the web page $2p8$ shown in FIG. 14 is performed. On this occasion, the ID key receiving portion 312 acquires the inputted ID key DTK and the electronic mail address ARD.

In the service providing site 3, the ID key DTK is used as a key for obtaining the private data DTH of the user from the information providing site 2.

Figure 15:
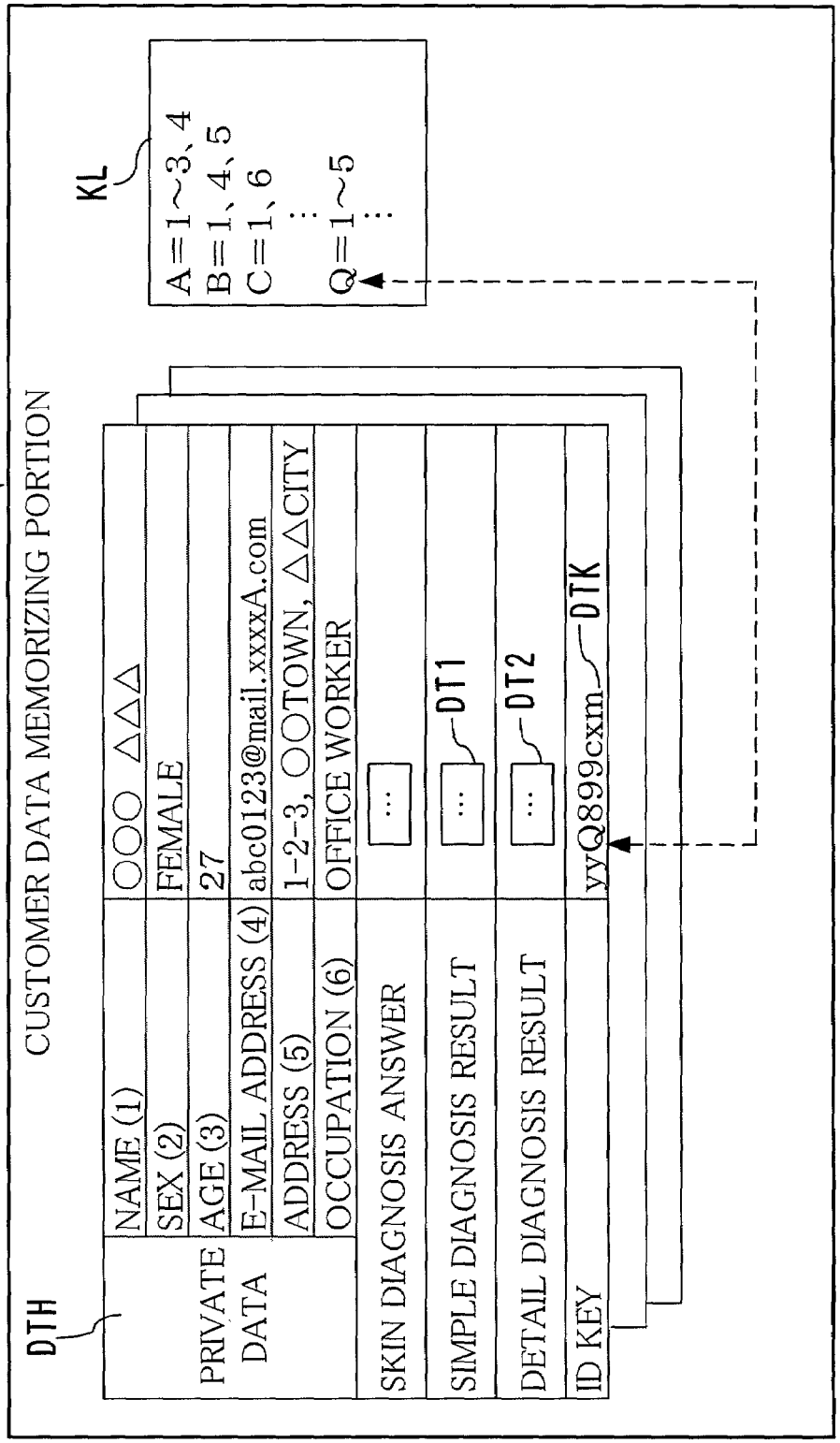
FIG. 15 is a diagram for explaining a customer data memorizing portion.

As shown in FIG. 15, since a character string such as "yyQ899cxm" in which alphanumeric characters and symbols are arranged at random is used for the ID key DTK, it is difficult for the service providing site 3 to fabricate the ID key DTK.

In addition, the ID key DTK is provided with a disclosable information DTHa concerning items of the private data DTH that can be disclosed to the service providing site 3. The customer data memorizing portion 212 has a disclosure item list KL, which memorizes numbers of the disclosable items for each disclosable information DTHa. For example, if the character "Q" in the "yyQ899cxm" is the disclosable information DTHa, it is considered that items "name", "sex", "age", "electronic mail address" and "address" can be disclosed to the service providing site 3 in accordance with "Q=1–5" in the disclosure item list KL.

Referring to FIG. 3 again, the customer data requesting portion 313 transmits the ID key DTK and the electronic mail address ARD obtained by the ID key receiving portion 312 to the information providing site 2, so as to request the simple diagnosis result DT1 and the private data DTH to the information providing site 2.

The customer data extracting portion 216 receives the ID key DTK and the electronic mail address ARD from the customer data requesting portion 313 and extracts the simple diagnosis result DT1 and the private data DTH corresponding to the ID key DTK from the customer data memorizing portion 212. In other words, the received ID key DTK and the ID key DTK memorized in the customer data memorizing portion 212 are compared with each other, and the simple diagnosis result DT1 and the private data DTH corresponding to the identical ID key DTK are obtained. Then, the extracted simple diagnosis result DT1 and the private data DTH are transmitted to the customer data receiving portion 314 of the service providing site 3. The received electronic mail address ARD is used for enhancing certainty of the comparison. Namely, the same process as in the verification where the ID key DTK is used is performed for the electronic mail address ARD, too. The address can be used instead of the electronic mail address, or only the ID key DTK can be used for the verification.

Figure 13:
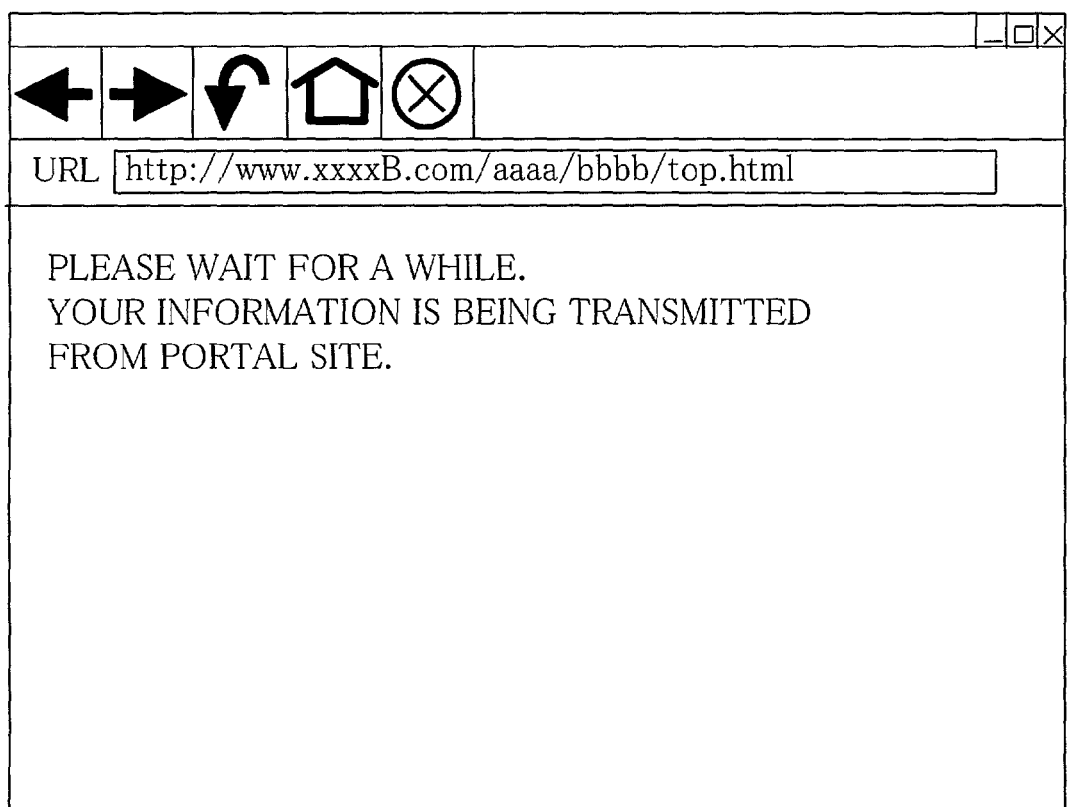
FIG. 13 shows an example of a web page for displaying that data are being transmitted.

The customer page generating portion 315 generates web pages that are customized for users in such a way as the web page $2p8$ shown in FIG. 14, in accordance with the simple diagnosis result DT1 and the private data DTH obtained by the customer data receiving portion 314 and the detail diagnosis result DT2 memorized in the detail result memorizing portion 316. The user can get access to the web page $2p8$ so as to get information about the product that is suitable for the user or to buy a product from the B-Company. If it takes a long time for forming the web page $2p8$, a message indicating that the data are being transmitted may be displayed as in the web page $2p9$ shown in FIG. 13.

According to this embodiment, the user who is a customer can receive products or services from the provider with an easy, and the provider can promote sales of products or services to users efficiently.

In this embodiment, the simple skin diagnosis and the detail skin diagnosis are performed one time for each. However, it is possible to perform only one skin diagnosis. It is also possible to perform the skin diagnosis three times or more, or the user may select the skin diagnosis to be performed.

Though the B-Company generates the detail diagnosis result DT2 of the detail skin diagnosis in this embodiment, a third party except the A-Company and the B-Company can perform the generation. In this case, the detail diagnosis result DT2 is transmitted from the third party to the A-Company. The B-Company may receive the detail diagnosis result DT2 together with the simple diagnosis result DT1 and the private data DTH from the information providing site 2.

Though the private data DTH is obtained by the skin diagnosis in this embodiment, the private data obtained by the information providing site 2 previously can be used. For example, if the user is a member of the information providing site 2, the information providing site 2 has the private data of the user. Therefore, if the obtained private data are used, the user may omit the input of data except the member ID when using the skin diagnosis. In addition, a data management that is efficient for the information providing site 2 can be performed.

A plurality of service providing sites 3 may be provided. For example, the service providing sites 3 are provided for the cosmetician B-Company and a drug maker C-Company, so that the B-Company and the C-Company can share the same diagnosis result. In this way, if the providers of different industrial categories share the same diagnosis result, each provider can expect a synergistic effect of sales promotion, while consumers can receive a provision of wide variety of products or services.

Furthermore, it is possible that a plurality of cosmetician companies share the same diagnosis result. Thus, each provider can activate the sales by competition between the providers, while consumers can receive the most suitable product or service by comparing products or services of the same type.

In this embodiment, the example of skin diagnosis of users for sales promotion of cosmetics are explained, but the present invention can be applied to other products or services. For example, concerning sales promotion of foods, a sample may be transmitted instead of the diagnosis kit 70 for testing the taste of the user.

The B-Company can use the obtained private data DTH for CTI (Computer Telephony Integration). For example, the obtained private data DTH are used when answering questions from the user via a telephone, a WWW browser, an electronic mail or a chat after selling a product to the user. The private data DTH makes it possible to answer questions from users directly without asking user's name, user's age or the product that the user bought. In this way, since the CTI enables the B-Company to respond to the user one to one, more thoroughgoing service can be provided.

The B-Company can provide a service providing site 3 as well as a site of a private brand Internet service (PBIS) that is special to users who bought products or services. For example, a member ID and an electronic mail address of a unique domain name for each of the users are issued. Then, information of a new product of the B-Company or a limited product is provided to the user via a private web page provided at the PBIS or the electronic mail that is transmitted to the electronic mail address. It is also possible to provide a bulletin board that is exclusive to members in the PBIS. In this way, the user who bought a product can be differentiated from other users, so as to gather more customers.

The information providing site 2 may be provided with a charging system. In general, an Internet service provider who provides a service of connecting the terminal device 4 to the Internet uses credit card payment system for collecting the service fee. Therefore, the information providing site 2 is provided with the charging system. The B-Company may ask the A-Company for collecting the price of the products under the contract with the A-Company. Thus, the provider does not need the charging system at the service providing site 3. Compared with the method of c.o.d. (collect on delivery), the nonpayment may be reduced. Since the customer is not required to make a new contract with a provider, the customer may not be in anxiety about leak of the credit card number.

It is possible that the user can receive payback of the detail skin diagnosis fee partially or entirely from the B-Company when inputting the ID key DTK in the text box TX7 of the web page 2*p*7 shown in FIG. 12 and transmitting the ID key DTK to the B-Company, i.e., when the user discloses the private data DTH to the B-Company. It is also possible that when buying a product or a service from the B-Company, the price is discounted. Thus, the number of users who utilize the event of the detail skin diagnosis may increase, resulting in effective sales promotion.

It is possible to use a plurality of servers 21 and 31 for realizing the functions of this embodiment.

Moreover, the structure, the process contents, the process order of the communication system 1, the information providing site 2 or the service providing site 3 can be modified partially or entirely in the scope of the present invention.

While the presently preferred embodiments of the present invention have been shown and described, it will be understood that the present invention is not limited thereto, and that various changes and modifications may be made by those skilled in the art without departing from the scope of the invention as set forth in the appended claims.

What is claimed is:

1. A communication system for communicating information between network sites that are connected to each other via a network, the system comprising:
 a first network site of a first entity that has a pre-established trusted relationship with the a user the first network site including
  a diagnosis unit performing a diagnosis of the user, who uses a terminal device on the network,
  a memory unit storing private information of the user and a diagnosis result of the diagnosis unit together in association with an ID key,
  an issue unit for issuing the ID key corresponding to the diagnosis result, the ID key being issued by the first network site and being used by a second network site of a second entity as a key for obtaining the private information of the user from the first network site, where the second entity does not have a trusted relationship with the user,
  a first transmission unit transmitting the diagnosis result and the ID key to the user, and
  a second transmission unit transmitting the private information and the diagnosis result to the second network site; and
 the second network site including
  an ID key reception unit receiving the ID key from the user,
  an ID key transmission unit transmitting the ID key received by the ID key reception unit to the first network site, and
  a user information reception unit receiving the private information corresponding to the ID key transmitted to the first network site and the diagnosis result from the first network site; wherein
 the second transmission unit transmits the private information corresponding to the ID key indicated by the second network site and the diagnosis result.

2. The communication system according to claim 1, wherein the ID key includes disclosable information concerning items of the private information that can be disclosed to the second network site, and the second transmission unit transmit only items of the private information corresponding to the disclosable information.

3. A communication system for communicating information between network sites that are connected to each other via a network, the system comprising:
 a first network site of a first entity including
  a memory unit storing private information of a user of a terminal device on the network together in association with an ID key,
  an issue unit for issuing the ID key corresponding to the diagnosis result, the ID key being issued by the first network site and being used by a second network site of a second entity as a key for obtaining the private information of the user from the first network site,
  a first transmission unit transmitting the ID key to the user, and
  a second transmission unit transmitting the private information to a second network site of a second entity; and
 the second network site of the second entity including
  a result transmission unit transmitting a result of a diagnosis performed for the user to the first network site,
  an ID key reception unit receiving the ID key from the user,
  an ID key transmission unit transmitting the ID key received by the ID key reception unit to the first network site, and
  a user information reception unit receiving the private information corresponding to the ID key transmitted to the first network site from the first network site; wherein the memory unit stores the diagnosis result received from the second network site together with the ID key, and the first transmission unit transmits the diagnosis result corresponding to the ID key, and the second transmission unit transmits the private information corresponding to the ID key presented by the second network site.

4. The communication system according to claim 3, wherein the ID key includes disclosable information concerning items of the private information that can be disclosed to the second network site, and the second transmission unit transmits only items of the private information corresponding to the disclosable information.

5. A communication system comprising:
a first network site of a first entity for giving information to a user of a terminal device that can be connected to a network, the first network site including
a diagnosis unit performing a diagnosis of the user for providing a product or a service,
a memory unit storing private information of the user and a diagnosis result of the diagnosis unit together in association with an ID key,
an issue unit for issuing the ID key corresponding to the diagnosis result, the ID key being issued by the first network site and being used by a second network site of a second entity as a key for obtaining the private information of the user from the first network site,
a first transmission unit transmitting the diagnosis result and the ID key to the user, and
a second transmission unit transmitting the private information and the diagnosis result to a second network site of a second entity; and
where the second network site is for giving information to the user for providing the product or the service, the second network site including
an ID key reception unit receiving the ID key from the user,
an ID key transmission unit transmitting the ID key received by the ID key reception unit to the first network site, and
a user information reception unit receiving the private information corresponding to the ID key transmitted to the first network site and the diagnosis result from the first network site; wherein
the ID key includes disclosable information concerning items of the private information that can be disclosed to the second network site, and the second transmission unit transmits only items of the private information corresponding to the disclosable information of the ID key indicated by the second network site.

6. A server that is used for an information providing network site for giving information to a user of a terminal device that can be connected to a network, the server comprising:
a diagnosis unit performing diagnosis of the user;
a memory unit storing private information of the user and a diagnosis result of the diagnosis unit together in association with an ID key;
an issue unit for issuing the ID key corresponding to the diagnosis result, the ID key being issued by the information providing network site and being used by a network site other than the information providing network site as a key for obtaining the private information of the user from the information providing network site,
a first transmission unit transmitting the diagnosis result and the ID key to the user; and a second transmission unit transmitting the private information and the diagnosis result to another network site, wherein the ID key includes disclosable information concerning items of the private information that can be disclosed to the other network site, and the second transmission unit transmits only items of the private information corresponding to the disclosable information of the ID key when the ID key is received from the network site other than the information providing network site.

7. An information agent method for mediating information between a consumer of a product or a service and a provider who provides the product or the service to the consumer using a computer and a network, the method comprising:
storing private information of the consumer;
acquiring a result of a diagnosis of the consumer for providing the product or the service;
issuing an ID key corresponding to the result, the ID key being for linking the result information and the private information and being used by the provider as a key for obtaining the private information of the consumer;
giving the diagnosis result and the ID key to the consumer; and
transmitting the private information corresponding to the ID key to the provider when the ID key obtained from the consumer is disclosed by the provider.
giving the diagnosis result and the ID key to the consumer; and
transmitting the private information corresponding to the ID key to the provider when the ID key obtained from the consumer is disclosed by the provider.

8. An information agent method performed between and for mediating information between a consumer of a product or a service and a provider who provides the product or the service to the consumer using a computer and a network, the method comprising:
passing a physical article received from the consumer, after it has been used by the consumer to the provider, who uses it to perform a physiological diagnosis;
obtaining a result of a diagnosis which is performed on the article by the provider;
storing private information of the consumer together in association with an ID key which can be used by the provider as a key for obtaining the private information of the consumer;
transmitting the diagnosis result and the ID key to the consumer; and
transmitting to the provider the private information corresponding to the ID key when the ID key is received from the provider.

9. A communication system for communicating information between network sites that are connected to each other via a network, the system comprising:
a first network site of a first entity including
a memory unit storing private information of a user of a terminal device on the network and a result of a diagnosis of the user together in association with an ID key,
an issue unit for issuing the ID key corresponding to the result, the ID key being issued by the first network site and being used by a second network site of a second entity as a key for obtaining the private information of the user from the first network site,
a first transmission unit transmitting the diagnosis result and the ID key to the user, and a second transmission unit transmitting the private information to a second network site of a second entity; and the second network site including an ID key reception unit receiving the ID key from the user, an ID key transmission unit transmitting the ID key received by the ID key reception unit to the first network site, and a user information reception unit receiving the private information corresponding to the ID key transmitted to the first network site from the first network site; wherein the first transmission unit transmits the diagnosis result corresponding to the ID key, and the second transmission unit transmits the private information corresponding to the ID key presented by the second network site.

10. A tangible computer-readable medium that can be read by a computer enabling the computer to function as a server used for an information providing network site that gives information to a user of a terminal device that can be connected to a network, the recording medium stores a program for making the computer execute a process including:

a diagnosis process of performing a diagnosis of the user a storing process of storing private information of the user and a diagnosis result of the diagnosis process together in association with an ID key;

an issue process of issuing the ID key corresponding to the diagnosis result, the ID key being issued by the information providing network site and being used by a network site other than the information providing network site as a key for obtaining the private information of the user from the information providing network site, a first transmission process of transmitting the diagnosis result and the ID key to the user; and a second transmission process of transmitting the private information designated by the ID key and the diagnosis result to a network site other than the information providing network site.

11. A computer program embodied on a storage and readable by a computer for enabling the computer to function as a server used for an information providing network site that gives information to a user of a terminal device execute the processes including:

a diagnosis process of performing a diagnosis of the user;

a storing process of storing private information of the user and a diagnosis result of the diagnosis process together with an ID key;

an issue process of issuing the ID key corresponding to the diagnosis result, the ID key being issued by the information providing site and being used by a network site other than the information providing network site as a key for obtaining the private information of the user from the information providing network site, a first transmission process of transmitting the diagnosis result and the ID key to the user; and a second transmission process of transmitting the private information designated by the ID key and the diagnosis result to another site.

12. An information agent method for a mediating entity to mediate information between a consumer of a product or a service and a third party provider who provides the product or the service to the consumer using a computer and a network, the method comprising:

storing, by the mediating entity, private information of the consumer including at least the personal identity of the consumer;

acquiring, by the mediating entity, a result of a physiological diagnosis of the consumer where the physiological diagnosis result is provided by the third party provider who performs a diagnosis using a kit from the consumer without being able to identify the consumer;

issuing, by the mediating entity, an ID key linking the physiological diagnosis result and the private information;

giving, by the mediating entity, the diagnosis result and the ID key to the consumer while withholding the ID key from the third party provider;

transmitting the private information corresponding to the ID key to the third party provider when the third party provider discloses the ID key, released by the consumer, to the mediating entity, where the third party provider uses the private information to market its product or service to the consumer.

* * * * *

UNITED STATES PATENT AND TRADEMARK OFFICE
CERTIFICATE OF CORRECTION

PATENT NO. : 7,054,929 B2
APPLICATION NO. : 09/893903
DATED : May 30, 2006
INVENTOR(S) : Hiroyuki Irie et al.

It is certified that error appears in the above-identified patent and that said Letters Patent is hereby corrected as shown below:

First Page Column 2 (Other Publication), Line 2, change "p." to --pp.--.

Column 11, Line 66, delete "a" before "user".

Column 14, Line 28, change "provider." to --provider,--.

Column 15, Line 25, after "user" insert --;--.

Column 16, Line 27, change "consumer' to --consumer,--.

Signed and Sealed this

Twelfth Day of December, 2006

JON W. DUDAS
*Director of the United States Patent and Trademark Office*